US00PP32825P3

(12) United States Plant Patent
Serrador

(10) Patent No.: US PP32,825 P3
(45) Date of Patent: Feb. 23, 2021

(54) STRAWBERRY PLANT NAMED 'A13-71'

(50) Latin Name: ***Fragaria* x *ananassa* Duch.**
Varietal Denomination: A13-71

(71) Applicant: Enríque Masiá Serrador, Lepe (ES)

(72) Inventor: Enríque Masiá Serrador, Lepe (ES)

(73) Assignee: MASIÁ CISCAR S.A., Lepe (ES)

( * ) Notice: Subject to any disclaimer, the term of this patent is extended or adjusted under 35 U.S.C. 154(b) by 0 days.

(21) Appl. No.: 15/932,970

(22) Filed: May 31, 2018

(65) Prior Publication Data

US 2019/0110385 P1 Apr. 11, 2019

Related U.S. Application Data

(60) Provisional application No. 62/604,134, filed on Jun. 22, 2017.

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./156, 208, 209
See application file for complete search history.

(56) References Cited

U.S. PATENT DOCUMENTS

PP26,874 P3 * 6/2016 Vinson ..... A01H 6/7409 Plt./208

* cited by examiner

*Primary Examiner* — Susan McCormick Ewoldt
*Assistant Examiner* — Karen M Redden
(74) *Attorney, Agent, or Firm* — Svendsen Legal, LLC

(57) ABSTRACT

A new day-neutral strawberry plant named 'A13-71' is disclosed, with exceptional yield and flavor characteristics.

4 Drawing Sheets

Genus and species: *Fragaria* x *ananassa* Duch.
Variety denomination: 'A13-71'.

STATEMENT REGARDING FEDERALLY SPONSORED RESEARCH OR DEVELOPMENT

None

BACKGROUND OF THE INVENTION

'A13-71' is a product of a breeding program carried out by the inventor in the Andalucia region of Spain. 'A13-71' was one of several seedlings resulting from an uncontrolled cross made in the year 2013. The seeds resulting from the uncontrolled cross with unknown parents were germinated indoors and the resulting seedling was transplanted to the trial seedling field. 'A13-71' was selected in the Andalucia region of Spain in the year 2014 based on observations of its fruiting characteristics. In 2015, 'A13-71' was asexually propagated by rooting stolons and was expanded to 30 plants which were planted in replicated trials in the Andalucia region of Spain. The plants were observed and evaluated, and the next year they were expanded for further observation and evaluation. The breeders of 'A13-71' have sold the variety commercially under the Trademark name Cleopatra WB or Cleopatra Circle R Brand. Contrast is made with the 'San Andreas' (U.S. Plant Pat. No. 19,97) in reference to the shape of the fruit; 'A13-71' presents an ovoid and globose shape while 'San Andreas' presents a conical shape. The color of the leaves of the 'San Andreas' variety is dark green while 'A13-71' variety has medium green leaves. The achenes of the fruit of 'San Andreas' are below the surface while those of 'A13-71' are at the same height as the surface.

Comparison is made with strawberry variety 'BG-4316' (U.S. Plant Pat. No. 23,255) known commercially in Europe as 'Victory'. The plants of 'A13-71' variety produce a yield of 670.52 g per plant while 'BG-4316' presents a higher yield of 810.66 g per plant. The fruit of 'A13-71' has a firmness of 400 in the penetrometer while 'BG-4316' variety has a greater firmness of 414 in the penetrometer. The fruit of 'A13-71' has a lower brix of 7.3 than 'BG-4316' which contains a brix of 7.6. The fruit of 'A13-71' is partially remontant allowing the variety to have a production with greater precocity than other varieties allowing the commercial use in different markets. 'A13-71' is commercialized primarily in the fresh fruit market and secondarily in the frozen fruit market. Throughout several generations of asexual propagation, 'A13-71' has been observed to retain its distinctive characteristics and remain true to type.

BRIEF DESCRIPTION OF THE PHOTOGRAPH

Figure 1:
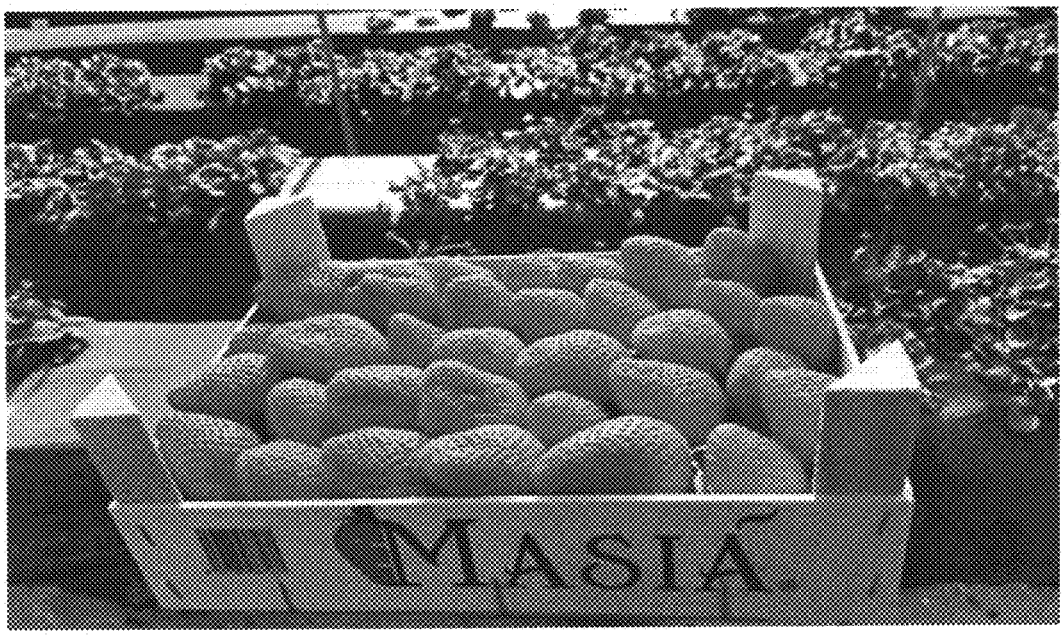
FIG. 1 illustrates 5-month-old strawberries of 'A13-71'.
Figure 2:
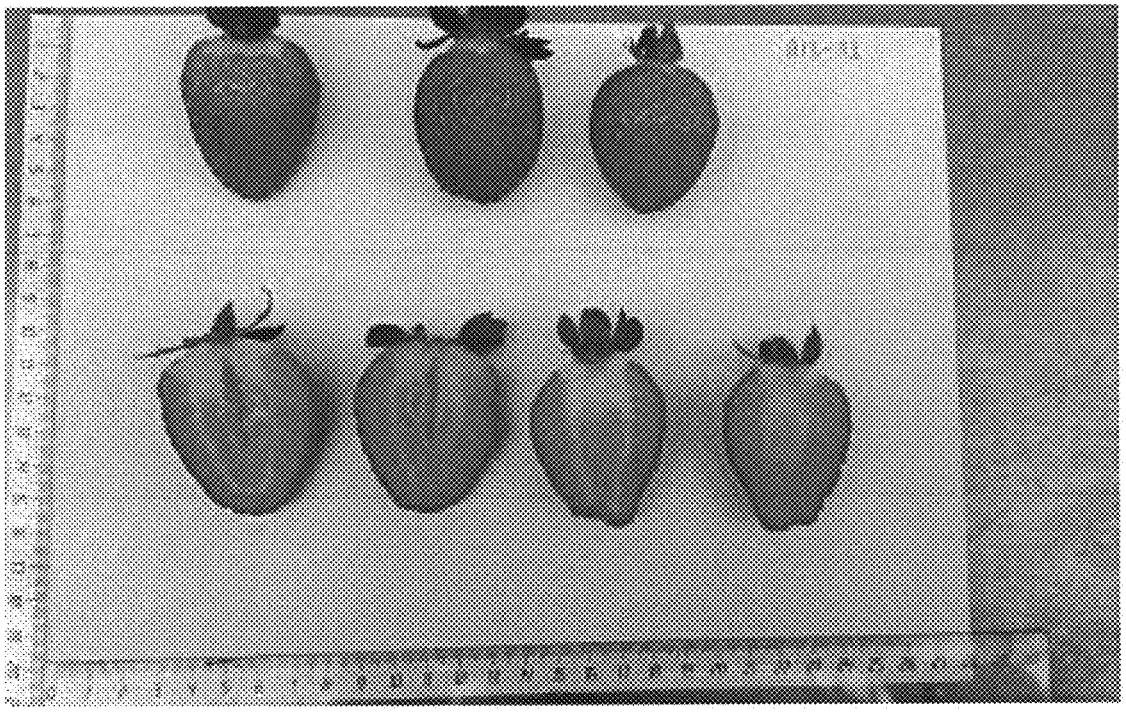
FIG. 2 illustrates individual whole berries and cross sections of whole berries of 5-month-old strawberries of 'A13-71'.
Figure 3:
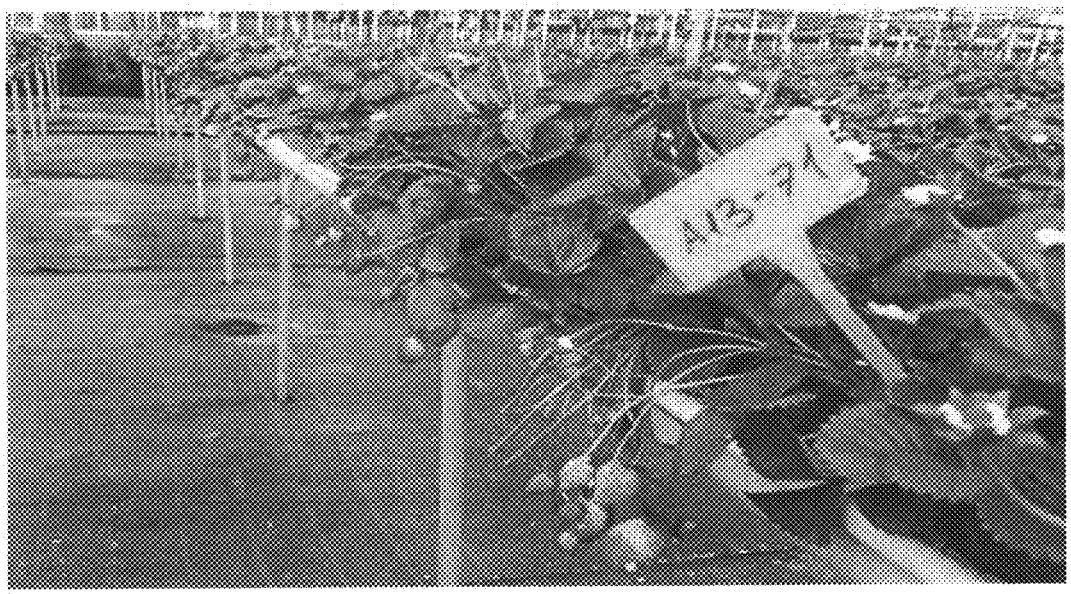
FIG. 3 illustrates 5-month-old plants of 'A13-71' growing in a raised bench system.
Figure 4:
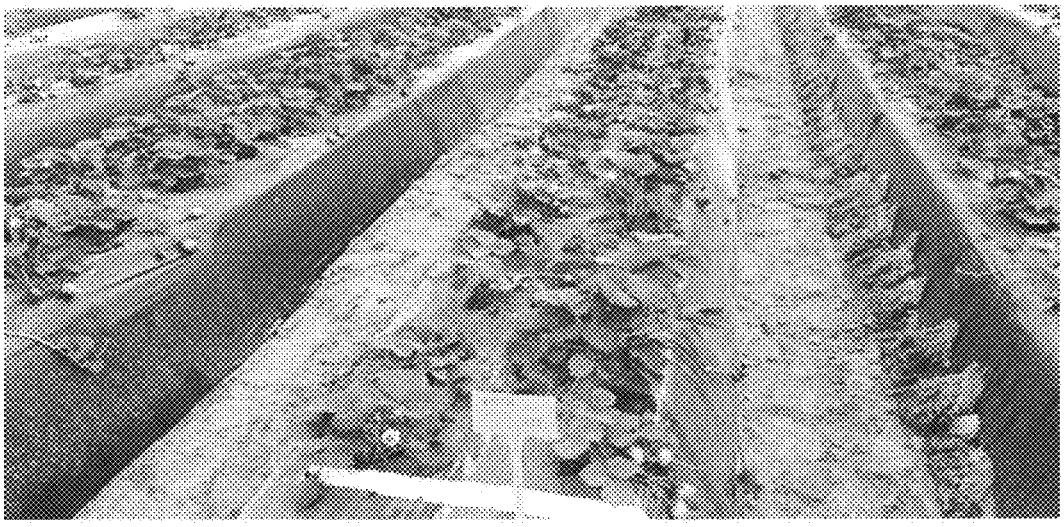
FIG. 4 illustrates 4-month-old plants of 'A13-71' growing in a traditional raised bed with black plastic mulch.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is that of a plant age of seven months and is based on observations made during the 2016 and 2017 growing seasons in the Andalucia region of Spain. It should be understood that the characteristics described will vary somewhat depending upon cultural practices and climatic conditions and can vary with location and season. Quantified measurements are expressed as an average of measurements taken from a number of individual plants of the new variety. The measurements of any individual plant or any group of plants, of the new variety may vary from the stated average. Color terminology follows The Royal Horticultural Society Colour Chart, London (R.H.S.) (Sixth Revised Edition, 2015).

General description:

*Ploidy*.—Octoploid.
*Blooming period*.—Approximately January through May in Huelva, Spain.
*Plant average height*.—26 cm.
*Plant average width*.—25 cm.
*Plant type*.—Herbaceous fruit producing perennial.
*Plant habit*.—Upright, semi-compact with dense canopy.
*Cold hardiness*.—Not tested in areas where temperatures of 32° F. occur.
*Root description*.—Fibrous, 10 days to initiate roots, 8 weeks to produce a rooted plant, Greyed-yellow group (162) Light yellow (C) in color.
*Propagation*.—Rooting of stolons.
*Growth rate*.—Vigorous.
*Stem*.—Acaulescent.

Stolons:

*Anthocyanin*.—Variable (absent to moderate).
*Average length*.—30-40 cm.
*Average diameter*.—4 mm.
*Average number*.—Variable, 25-35 stolons.
*Color*.—Yellow-green group (144) Light yellow green (D).

Foliage description:

*Average leaf length*.—8 cm.
*Average leaf width*.—14 cm.
*Leaf texture* (*both surfaces*).—Moderately soft (both).
*Leaf pubescence*.—Medium.
*Leaf division*.—Three leaflets.
*Leaf arrangement*.—Basal.
*Leaf attachment*.—Petiolate.
*Terminal leaflet average length*.—8 cm.
*Terminal leaflet average width*.—6.5 cm.
*Terminal leaflet pubescence density*.—Medium.
*Terminal leaflet texture* (*both surfaces*).—Moderately soft (both).
*Leaflet shape*.—Broadly ovate to rounded.
*Leaflet margins*.—Serrate, slightly pointed to slightly rounded.
*Leaflet base*.—Asymmetrically oblique and rounded.
*Leaflet apex*.—Round.
*Leaflet venation*.—Pinnate, coloration matched leaflet color.
*Leaflet color*.—Upper surface Green group (143) Strong yellow green (B), lower surface Green group (143) Moderate yellow green (D), no variegation present on either surface.

Petiole:

*Petiole*.—Round in shape, strong in strength.
*Average length*.—15 cm.
*Average diameter*.—3 mm.
*Pubescence*.—Low or medium.
*Pubescence density*.—Moderate.
*Pose of hairs*.—Variable.
*Texture*.—Moderately soft.
*Anthocyanin*.—Absent.
*Color*.—Yellow-green group (145) Light yellow green (B).

Petiolule:

*Petiolule*.—Round in shape.
*Average length*.—Terminal leaflets 10 mm, Lateral leaflets 5 mm.
*Average diameter*.—2 mm.
*Color*.—Yellow-green group (145) Light yellow green (B).

Stipule:

*Average length*.—22 mm.
*Average width*.—12 mm.
*Color*.—Yellow-green group (145) Light yellow green (C).

Flower description:

*Average size* (*diameter*).—35 mm.
*Average number of flowers*.—4-6 flowers per cluster.
*Inflorescence*.—Truss.
*Flower initiation and expression conditions*.—Temperature and day-length dependent.
*Time of flowering* (50% *of plants at first flower*).—Early to mid-season.
*Flower fragrance*.—Slight.

Sepal:

*Average length*.—10 mm.
*Average diameter*.—5 mm.
*Texture* (*both surfaces*).—Partially soft.
*Color*.—Yellow-green group (146) moderate yellow green (D).
*Sepal position*.—Mixed arrangement relative to the fruit.

Petals:

*Petals*.—Round in shape, obtuse base and apex, slightly overlapping, entire margins.
*Average number*.—5.
*Average length*.—9 mm.
*Average width*.—10 mm.
*Texture*.—Soft.
*Color*.—White Group (NN155) White (D).

Peduncle:

*Peduncle*.—Strong in strength.
*Average length*.—35-40 cm.
*Average diameter*.—4 mm.
*Color*.—Yellow-green group (145) Light yellow green (B).

Pedicel:

*Pedicel*.—Strong in strength.
*Average length*.—6-10 cm.
*Average diameter*.—2 mm.
*Color*.—Yellow-green group (145) Light yellow green (B).
*Pistils*.—Average of 145, average of 1.1 mm in length, steeply dome shaped, Yellow-green group (153) Strong yellow (D).
*Stigma color*.—Yellow-green group (153) Strong yellow (D).

*Style color*.—Yellow-green group (153) Strong yellow (D).

*Stamens average length*.—1.5 mm.

*Stamens*.—Average of 26, Yellow-green group (153) Strong greenish yellow (C), pollen is moderate in quantity and Vivid Greenish Yellow 2A in color.

*Bracts*.—Observed on the majority of the flower trusses from early developmental stage, which progresses into a typical single leaflet as the truss matures and fruit develops with characteristics similar to leaflets.

Fruit description:

*Shape*.—Primarily ovoid to globose, shape is similar for primary, secondary, and tertiary fruit.

*Season of harvest*.—January through May in Huelva, Spain.

*Time of ripening* (50% *of plants with first ripe fruit*) .—Early.

*Time of bearing*.—Day-Neutral, It will flower independent of day length.

*Average length of fruit*.—3-5 cm.

*Average width of fruit*.—2-5 cm.

*Weight of primary fruit*.—20-35 g.

*Weight of secondary and tertiary fruit*.—15-25 g.

*Fruit cavity*.—Absent or small.

*Surface*.—Smooth and glossy.

*Glossiness*.—Even and very high.

*External color* (*skin*).—Orange-red group (32) vivid reddish Orange (A), color is retained throughout the cropping season and holds up well to high seasonal temperatures.

*Internal color*.—Orange-red group (33) vivid reddish Orange (B).

*Evenness of color of skin*.—Even.

*Acidity*.—Low.

*Sweetness*.—High, brix 7.3.

*Firmness*.—Skin is very firm (resistant to bruising), flesh is moderately firm, 400 on the penetrometer.

*Juiciness*.—Moderate.

*Aroma*.—High.

*Weight*.—Average of 670.52 g per plant.

*Shelf life*.—An average of 8 to 10 days.

*Achene*.—Orange-red group (31) Strong reddish Orange (A) on the shady side, Orange-red group (30) vivid reddish Orange (A) on the sunny side.

*Achene number*.—An average of 250 per berry.

*Achenes*.—Same height as the surface.

*Disease and pest resistance*.—The 'A13-71' variety is sensitive to aphids, including *Aphis gossypii*. It has a certain tolerance to the red spider *Tetranychus urticae*.

The invention claimed is:

1. A new and distinct strawberry plant as shown and described herein.

* * * * *